United States Patent [19]

Harris

[11] Patent Number: 4,557,722
[45] Date of Patent: Dec. 10, 1985

[54] FILL PORT FOR AN IMPLANTABLE DISPENSING SYSTEM

[75] Inventor: Donald L. Harris, Miami Beach, Fla.

[73] Assignee: Cordis Corporation, Miami, Fla.

[21] Appl. No.: 484,571

[22] Filed: Apr. 13, 1983

[51] Int. Cl.[4] .................................. A61M 31/00
[52] U.S. Cl. ................................ 604/9; 604/891
[58] Field of Search ............... 128/D12; 604/9, 131, 604/134, 151–153, 169, 174, 256, 891; 251/149.8, 149.6, 353, 349

[56] References Cited

U.S. PATENT DOCUMENTS

| | | | |
|---|---|---|---|
| 3,148,700 | 9/1964 | Friedell | 251/322 |
| 3,853,127 | 12/1974 | Spademan | 604/167 |
| 4,019,499 | 4/1977 | Fitzgerald | 128/1 R |
| 4,265,241 | 5/1981 | Portner et al. | 128/D12 |
| 4,334,551 | 6/1982 | Pfoster | 251/149.8 |
| 4,354,523 | 10/1982 | Hochmuth et al. | 251/149.6 |
| 4,360,019 | 10/1982 | Portner et al. | 604/891 |

Primary Examiner—C. Fred Rosenbaum
Assistant Examiner—Karen Kaechele
Attorney, Agent, or Firm—Lockwood, Alex, Fitzgibbon & Cummings

[57] ABSTRACT

An implantable medication dispensing system includes an integral reservoir from which medicament is dispensed by a manually actuated micro-infusion pump system. Medicament is added to and removed from the reservoir as required through a liquid-sealed fill port having a integral needle-actuated safety valve. Upon introduction of the needle through a self-sealing septum, the safety valve is actuated open to allow medicament to be introduced and withdrawn by the needle. Upon removal of the needle the septum is closed by radial compression and the safety valve is actuated closed to prevent pressure flow through the fill port.

10 Claims, 6 Drawing Figures

FILL PORT FOR AN IMPLANTABLE DISPENSING SYSTEM

BACKGROUND OF THE INVENTION

The present invention is directed generally to infusion systems, and more particularly to an implantable fill port having an internal needle-actuated safety valve for introducing medicament to a subcutaneous reservoir.

Implanted manually-actuated micro-infusion pump systems are advantageously employed when specific dosages of a medicament are to be administered within the human body at various times over an extended time period, as in the treatment of diabetes and other diseases of the digestive system.

In the treatment of diabetes a dispensing system comprising a combined pump and medicament reservoir system is subcutaneously implanted in soft tissue close to the delivery site, such as over the peritoneum and abdominal muscles, and a catheter is utilized to deliver insulin to the site. Alternatively, the reservoir is implanted remotely from the site and connected to a pump system by means of a flexible catheter. When insulin is required actuation of the pump system is accomplished by the patient applying pressure on the skin surface overlying the pump.

Typically, medicament is added to the reservoir at periodic intervals through a fill port provided in the wall of the reservoir. A hypodermic needle is inserted through the skin so as to contact and puncture a needle penetrable fluid impermeable membrane included in the port. All remaining medicament is then withdrawn, and a new known volume of medicament is introduced through the needle.

One drawback of previous implantable fill ports was their susceptibility to leakage when fluid in the associated reservoir was subjected to an applied pressure. This problem became more pronounced with repeated use of the fill port, since repeated puncturing of the fill port septum by the hypodermic needle weakened or decreased the effectiveness of the sealing membrane.

The present invention overcomes this problem by incorporating within the fill port an integral needle-actuated valve. Upon introduction of the needle through the septum of the port the valve is automatically opened to allow the addition or withdrawal of the medicament. Upon removal of the needle the valve automatically closes, and by reason of the construction of the valve increased pressure within the reservoir enhances the sealing properties of the valve. Also, in accordance with another aspect of the invention, the septum may be maintained under compression to preclude leakage through the septum upon removal of the needle.

Accordingly, it is a general object of the present invention to provide a new and improved fill port for implantable dispensing systems.

It is a more specific object of the present invention to provide a new and improved fill port which is less susceptible to leakage from internally applied medicament pressure.

It is a more specific object of the present invention to provide a new and improved implantable fill port which opens upon introduction of a needle, and is automatically closed upon removal of the needle.

SUMMARY OF THE INVENTION

The present invention is directed to an implantable fill valve system for a fluid reservoir which includes a housing defining a valve chamber. A needle-penetrable fluid-impermeable membrane is disposed at one end of the chamber. Fluid communication between the valve chamber and the reservoir is established by a valve disposed for operative engagement with the needle upon the needle entering the port housing through the membrane to facilitate removal or introduction of medicament from the reservoir.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
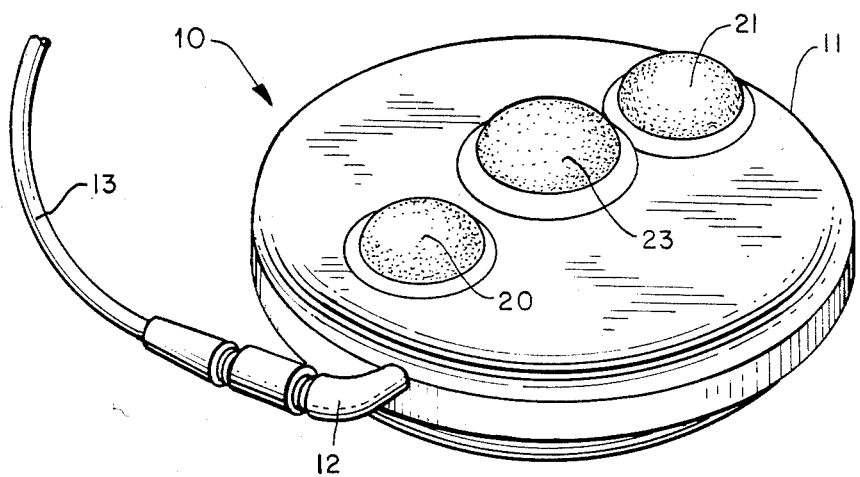
FIG. 1 is a perspective view of a combined pump and reservoir fluid dispensing system incorporating a fill port constructed in accordance with the invention.
Figure 2:
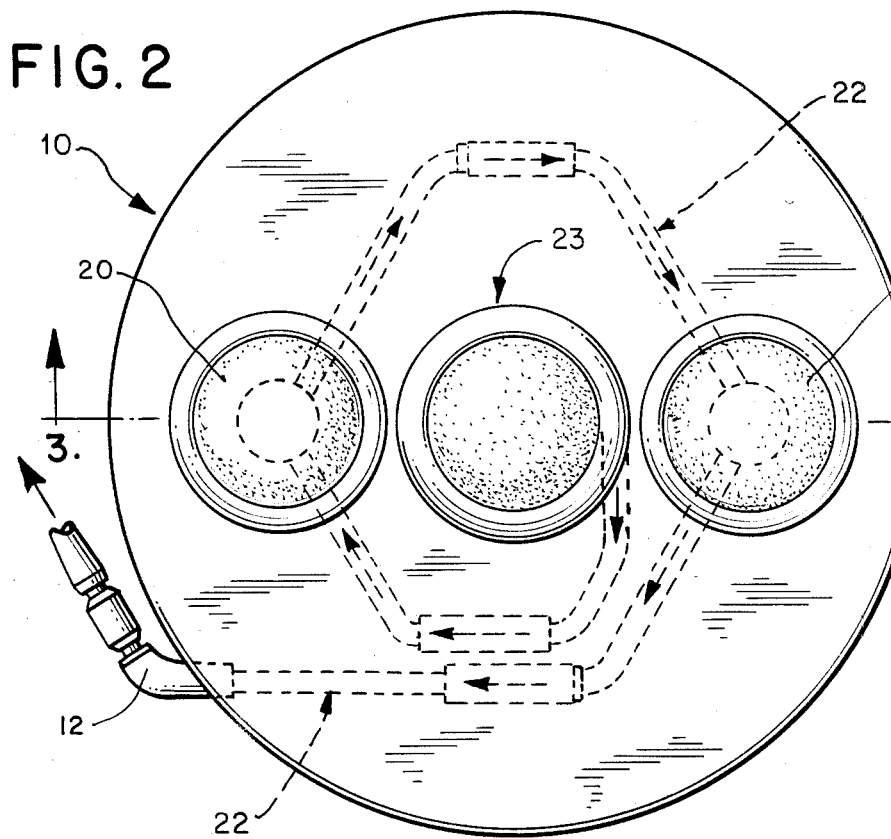
FIG. 2 is an enlarged top plan view of the dispensing system of FIG. 1 illustrating the fluid circuit and fill port contained therein.

Referring to the drawings, and particularly to FIGS. 1-4, a fill port constructed in accordance with the invention may be advantageously utilized in an implantable combined pump and reservoir medicament dispensing system 10. As seen in FIG. 1, this dispensing system includes a generally disc shaped housing 11 within which pump, reservoir and fill port elements are contained, and a dispensing port 12 from which medicament is dispensed to an administration site by means of a flexible catheter 13 of conventional construction. The dispensing system 10 is preferably of compact construction for implantation with minimal distress to the human body.

Figure 3:
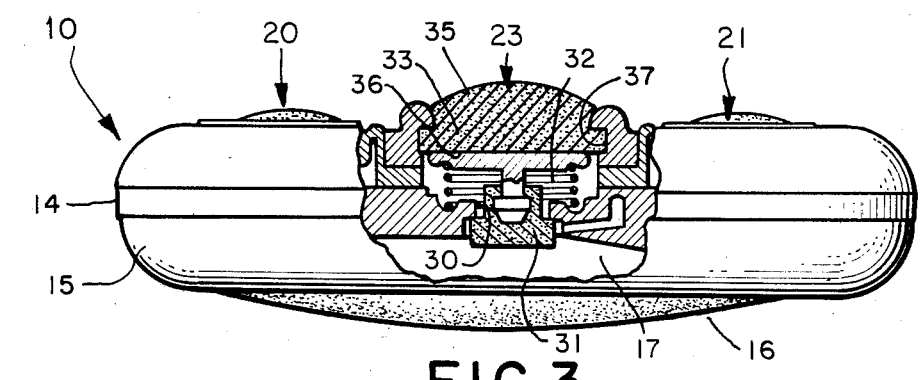
FIG. 3 is a cross-sectional view of the dispensing system taken along line 3—3 of FIG. 2.

Referring to FIG. 3, housing 11 is seen to include a base portion 14, which may be formed of a hard biocompatible material such as plastic, and an overlying body portion 15, which may also be formed of a biocompatible material such as a similar plastic. The body portion defines a recess over which a flexible and expandable wall 16 of Dacron reinforced siliastic material is provided to form an internal reservoir 17 within which a volume of medicament is to be dispensed is stored.

To provide for the reliable dispensing of accurate dosages of medicament from reservoir 17, dispensing system 10 includes a safety pump 20 and a metering pump 21. These pump components, which are manually actuated by the application of pressure to the exterior surface of the dispensing system, are interconnected within housing 11 by means of a fluid circuit 22 such that upon actuation of safety pump 20 medicament (or other fluid in the reservoir of dispenser 10) passes from the reservoir to the metering pump 21. Then, upon actuation and release of the metering pump 21 the medicament is dispensed through dispensing port 12 to the delivery site. The construction and operation of this pump system is described in the copending application of the present applicant entitled "Implantable Manually Operated Medication Dispensing System", Ser. No. 484,572 filed Apr. 13, 1983.

Dispensing system 10 includes, in accordance with the invention, a fill port 23 through which medicament may be added to or removed from reservoir 17. This fill port, which is positioned generally in the center of housing 11 between the safety pump 20 and the metering pump 21, allows convenient subcutaneous fluid communication with reservoir 17 by means of a single needle, while providing reliable protection against pressure induced leakage from the reservoir.

Figure 4:
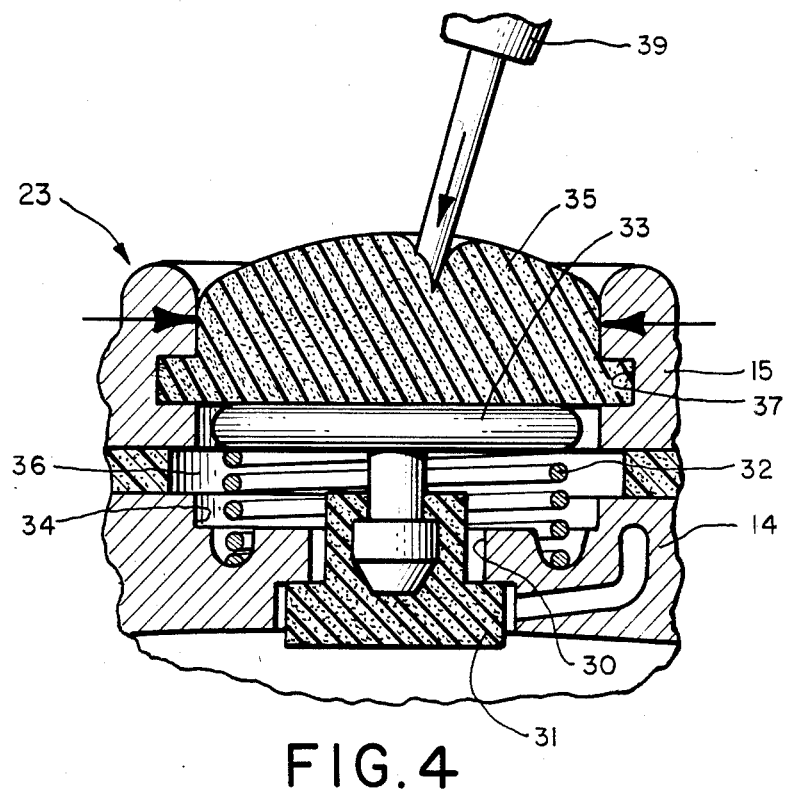
FIG. 4 is an enlarged cross-sectional view of the fill port showing the port in a closed condition prior to introduction of a needle.

Basically, as shown in FIGS. 3 and 4, fill port 23 is formed in part by an aperture 30 in base member 14 of housing 11. A valve member 31 extends through this aperture and includes an annular valving surface which engages a valve seat formed by the aperture to control flow through the aperture. The valving member 31 is biased to a closed position by a helical spring 32 which bears against a valve actuator member 33 in mechanical engagement with valving member 31. An annular channel 34 is provided in base member 24 to receive the spring 32. An overlying needle-penetrable fluid-impermeable septum 35 formed of a bio-compatible rubber of silastic material is held in compressive engagement by the molded body portion 15 to provide a fluid-sealed chamber 36. An annular channel 37 may be formed around the inside perimeter of chamber 36 to assist in the sealing engagement, the interior diameter of the chamber across the channel preferably being less than the exterior diameter of septum 35 to maintain the septum in radial compression relative to its axis for improved fluid sealing.

As shown in FIG. 4, fill port 23 is normally closed, the valve member 31 being biased by spring 32 against the valve stop. Pressure exerted by the medicament in reservoir 17, as shown by the arrows, only serves to more firmly seat valve member 31, thereby preventing uncontrolled medicament flow through the fill port. The needle-penetrable septum 35, being held firmly in radial compression within the annular rim 37 of housing member 15, further serves to maintain a liquid seal against fluids internal or external of the dispensing system 10.

Figures 5A, 5B:
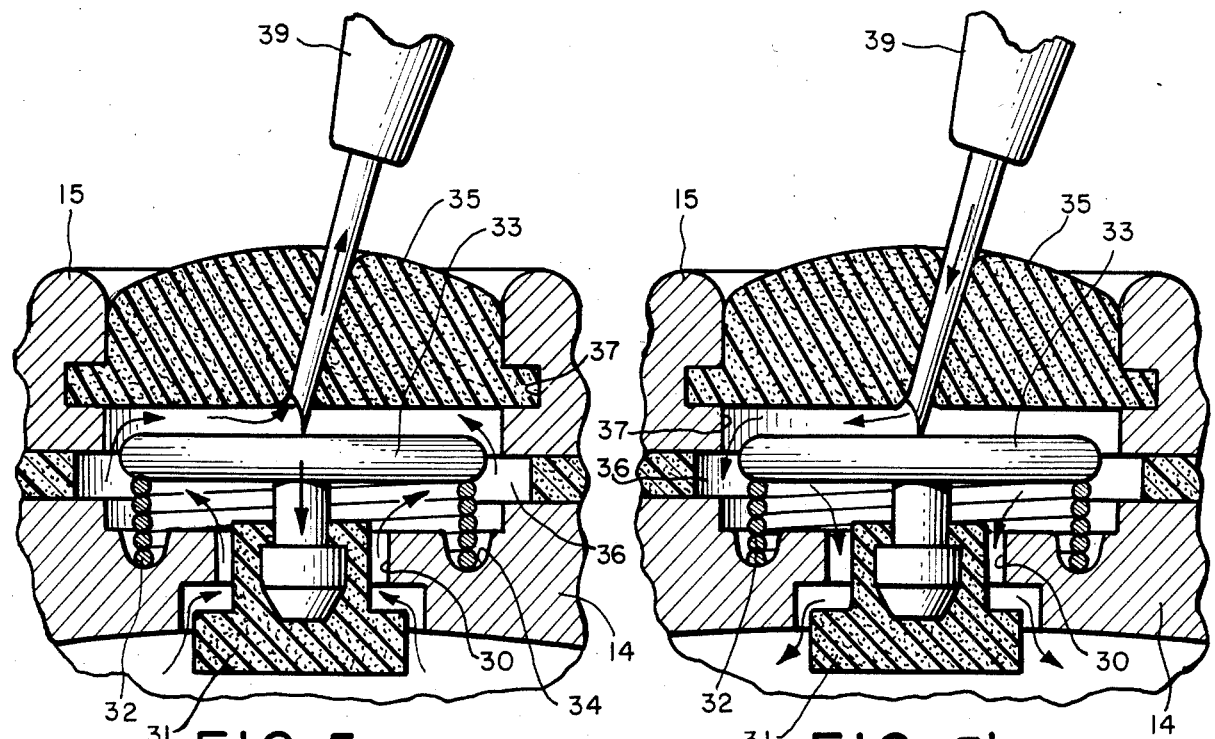
FIG. 5a is a view of the fill port subsequent to introduction of the needle showing the port in an open condition and medicament being introduced into the reservoir.
FIG. 5b is a view of the fill port similar to FIG. 5a showing medicament being withdrawn from the reservoir.

Referring to FIG. 5a, upon introduction of a needle 39 through septum 35, actuator member 33 is forced downwardly upon contact with the needle. This causes valve member 31 to be displaced from its valve seat, opening aperture 30 and establishing fluid communication between reservoir 17 and port chamber 36.

Generally, prior to introducing new medicament, the remaining medicament within reservoir 17 is withdrawn through needle 39 to prepare the reservoir for receiving a new and known volume of medicament. After the medicament has been thus withdrawn from the reservoir, new medicament may be introduced through the same needle 39 (or through a different needle inserted through septum 35) until the reservoir has been refilled to the desired volume.

The new medicament introduced through needle 39 enters the reservoir through aperture 30, as shown in FIG. 5b. The valve member 31 remains depressed by the force of needle 39 on actuator member 33.

Upon completion of the filling procedure, needle 39 is removed. This allows spring 32 to return valve member 31 to its closed position, effectively closing aperture 30 to prevent further fluid flow into or out of reservoir 17. At the same time, the compressive force exerted by housing member 15 on septum 35 causes that component to reseal as the needle is withdrawn, so that an additional liquid-tight seal exists across the top surface of the fill port.

It will be appreciated that the fill port of the invention, although shown in conjunction with a combined reservoir and pump medicament dispensing system, can be utilized in conjunction with virtually any implanted reservoir or catheter to permit the subcutaneous introduction of fluids. For example, the fill port of the invention may be utilized in conjunction with an implanted electrically actuated pump systems utilized for diabetes treatment.

While a particular embodiment of the invention has been shown and described, it will be obvious to those skilled in the art that changes and modifications may be made therein without departing from the invention in its broader aspects, and therefore, the aim in the appended claims is to cover all such changes and modifications as fall within the true spirit and scope of the invention.

I claim:

1. A bi-directional fill port for use in conjunction with a hypodermic needle for emptying and filling a subcutaneous fluid reservoir, comprising:

a housing defining a valve chamber having a first aperture, and a second aperture generally opposite said first aperture in fluid communication with the reservoir;

a fluid-impermeable needle-penetrable septum overlying said first aperture;

normally-closed valve means having a biasing means and including a valve member and cooperating valve seat exterior to said chamber for selectively closing said second aperture, said valve member including a stem portion extending through said second aperture into said chamber and a needle-engaging actuator portion within said chamber arranged for engagement by the needle upon insertion of the needle through said septum, said valve member being actuable open by the needle from within said chamber upon the needle coming into operative engagement with said engaging portion.

2. A fill port as defined in claim 1 wherein said valve stem is spring-biased against said valve seat.

3. A fill port as defined in claim 2 wherein said actuator portion substantially underlies said septum within said valve chamber.

4. A fill port as defined in claim 1 wherein said valve chamber is generally cylindrical, said septum is located at one end thereof, and said valve means are located at the other end thereof.

5. A fill port as defined in claim 4 wherein said septum is maintained in uniform radial compression about its circumference by said housing.

6. A fill port as defined in claim 2 wherein said valve means include a helical spring within said valve chamber for biasing said valve stem into engagement with said valve seat.

7. A bi-directional fill port for establishing bi-directional fluid communication between a subcutaneous fluid reservoir and a hypodermic needle, comprising:
 a housing defining a valve chamber having a first aperture, a second aperture generally opposite said first aperture in fluid communication with the reservoir;
 means including a fluid-impermeable needle-penetrable septum extending over said first aperture for forming a needle-penetrable liquid seal; and
 valving means including a valve seat concentric to said second aperture exterior to said valve chamber, and a reciprocatively-mounted valve member operatively engaged by a biasing means, with said valve seat exterior to said chamber for liquid-sealing said second aperture, said valve member including a stem portion extending through said second aperture into said chamber and an actuator portion within said chamber arranged for operative engagement with the needle upon the needle piercing said membrane and extending through said first aperture whereby said valve member is displaced from said valve seat by the needle to establish bi-directional fluid communication between said valve chamber and the reservoir through said second aperture.

8. A fill port as defined in claim 7 wherein said valve chamber is generally cylindrical, said septum is located at one end thereof, and said valve means are located at the other end thereof.

9. A fill port as defined in claim 7 wherein said septum is maintained in uniform radial compression about its circumference by said housing.

10. A fill port as defined in claim 7 wherein said valve means include a helical spring within said valve chamber for biasing said valve stem into engagement with said valve seat.

* * * * *